United States Patent
Ward

(10) Patent No.: US 9,517,183 B2
(45) Date of Patent: Dec. 13, 2016

(54) NIPPLE ABRASION PROTECTOR

(71) Applicant: Patrick B. Ward, Owensboro, KY (US)

(72) Inventor: Patrick B. Ward, Owensboro, KY (US)

( * ) Notice: Subject to any disclaimer, the term of this patent is extended or adjusted under 35 U.S.C. 154(b) by 454 days.

(21) Appl. No.: 13/815,103

(22) Filed: Jan. 30, 2013

(65) Prior Publication Data

US 2013/0228186 A1 Sep. 5, 2013

Related U.S. Application Data

(60) Provisional application No. 61/632,709, filed on Jan. 30, 2012.

(51) Int. Cl.
*A61F 13/14* (2006.01)
*A61J 13/00* (2006.01)
*A61F 13/15* (2006.01)

(52) U.S. Cl.
CPC ............... *A61J 13/00* (2013.01); *A61F 13/14* (2013.01); *A61F 2013/15016* (2013.01)

(58) Field of Classification Search
CPC ....................................................... A61J 13/00
See application file for complete search history.

(56) References Cited

U.S. PATENT DOCUMENTS

| | | | |
|---|---|---|---|
| 2,364,866 A * | 12/1944 | Meynier, Jr. ............ | A61J 13/00 128/890 |
| 2,448,938 A * | 9/1948 | Wayne .................... | A61J 13/00 604/346 |
| 4,333,471 A | 6/1982 | Nakai | |
| 4,640,288 A | 2/1987 | Hattori | |
| 5,032,103 A * | 7/1991 | Larsson ................ | A61F 15/008 128/890 |
| 5,171,321 A * | 12/1992 | Davis ........................ | A61F 2/52 128/890 |
| 5,669,395 A | 9/1997 | Thompson | |
| 5,690,536 A * | 11/1997 | Madden ................ | A61F 13/141 2/267 |
| 5,782,672 A | 7/1998 | Woodley | |
| 5,843,062 A * | 12/1998 | Reidmiller ............ | A61F 13/141 604/378 |
| 6,350,175 B2 | 2/2002 | Johnson | |
| 6,695,678 B1 * | 2/2004 | Foley .................. | A61F 13/8405 2/267 |
| 6,857,935 B1 | 2/2005 | Dohan | |
| 7,487,779 B2 | 2/2009 | Kurz | |
| 7,566,344 B2 | 7/2009 | Hansen | |

(Continued)

*Primary Examiner* — Tarla Patel
(74) *Attorney, Agent, or Firm* — Carrithers Law Office PLLC

(57) ABSTRACT

A nipple abrasion protector consists of a generally disc-shaped translucent polymeric adhesive film with adhesively affixed to one side of a release paper. The protector is removed from the paper and applied to the nipple to prevent chafing from contact with a shirt or other garment during extended physical activities like running and is semi-transparent or translucent and not readily detectable during activities like swimming or surfing. In addition, the protector is perforated with pores for breathablilty and has a cross-hatched surface texture to improve adhesion and flexibility. Moreover, the removable nipple protector adheres tightly to the areola and is capable of resisting protrusion of the nipple. The protector is free from materials such as latex which may incite an allergic reaction.

14 Claims, 3 Drawing Sheets

(56) References Cited

U.S. PATENT DOCUMENTS

| | | | |
|---|---|---|---|
| D601,305 S | 9/2009 | Bryan | |
| 7,921,851 B2 | 4/2011 | Kurz | |
| 8,628,507 B1 * | 1/2014 | Carroll | A61F 13/141 604/346 |
| 2003/0014108 A1 * | 1/2003 | Lauren | A61F 2/52 623/7 |
| 2005/0119631 A1 * | 6/2005 | Giloh | A61F 13/512 604/367 |
| 2005/0239369 A1 * | 10/2005 | Clark | A61F 13/141 450/81 |
| 2008/0071370 A1 | 3/2008 | Vinas | |

* cited by examiner

NIPPLE ABRASION PROTECTOR

CROSS REFERENCES TO RELATED APPLICATIONS

This application claims priority from U.S. Provisional application Ser. No. 61/632,709 filed on Jan. 30, 2012 which is incorporated by reference herein.

TECHNICAL FIELD

The present invention relates to an article of apparel and more particularly to a device for protecting and concealing the nipple of a man's or a woman's breast.

BACKGROUND OF THE INVENTION

Many men and women lead an active life style which includes exercise and sports activities. The clothing worn during these activities sometimes causes painful chafing and even abrading of the skin on various areas of the body. Especially prone to chafing and abrading arc the nipples due to their protruding out from the breasts. For example, during long runs, runners have experienced severe chafing and even bleeding of the nipples. The constant motion of the shirt or other upper body garment against the nipples causes discomfort, pain and skin abrasions in the particularly tender area at the end of the nipples.

Another issue related to sporting activities or exercise is the appearance caused by the protruding of nipples through women's exercise outfits or a bathing suits. Many women prefer a modest appearance which requires the absence of any protrusion due to nipples in a garment worn on the chest.

Further, the fashions of the day in women's wear are more casual and sensual but still require a measure of modesty which is provided by the present invention wherein the presence of a protruding woman's nipple through selected apparel is prevented. Additionally, women normally wear a brassiere to provide support and a pleasing contour under selected apparel. However, during hot summer months, when wearing lighter and thinner apparel, a brassiere will show through in an undesirable manner. For this reason as well as the discomfort involved in wearing a brassiere in hot weather, a woman may Choose not to wear a brassiere. In this situation, however, it is highly desirable to prevent the protruding of nipples through light or thin garments.

DESCRIPTION OF THE RELATED ART

U.S. Pat. No. 4,333,471 by Nikki for NIPPLE Protector issued on Jun. 8, 1982, teaches a flexible and air permeable paper disc with a pressure sensitive adhesive and a smaller central disc shaped padded material without adhesive, and a piece of release paper which protector s the central pad and is removably adhered to the flexible paper disc. The release paper is removed prior to use and then discarded. The present invention does not require and therefore does not include a central pad. Further, the present invention consists of just one disc-shaped layer of tape like material with adhesive and a piece of release paper. Containing only one layer of material, the present invention gives a more preferable flatter appearance than a protector which includes a central pad.

U.S. Pat. No. 5,782,672 for NIPPLE PAD by Woodley teaches a nipple pad including a pliable protector, a centrally located padded liner, adhesive strips and a release liner. Adhesive only appears near the outer marginal edge of the nipple pad. The present invention does not required and therefore does not include a central pad. As mentioned in the paragraph above, the present invention consists of just one disc-shaped layer of tape like material with adhesive and a piece of release paper which is peeled from the adhesive layer and discarded. Containing only one layer of material, the present invention gives a more preferable flatter appearance than a protector which includes a central pad.

SUMMARY OF THE INVENTION

In accordance with the present invention, there is provided a nipple abrasive protector for covering and protecting the nipples of a user from chafing during due to contact of a garment with the wearer's nipple. The protector comprises a cover composed of a polymeric material depicting a disc-shaped base member sized to cover the areola or portion thereof including protecting the marginal area around the nipple. The protector is comprises a film having indentations formed by creasing the film with closely spaced apart parallel ridges in a selected orientation, for example along a horizontal plane together with oppositely aligned spaced apart ridges formed normal or perpendicular to in a vertical plane forming a criss-cross pattern to provide strength and durability and flexibility to the protector. The ridges can be offset in other patterns or even formed as circles so long as ridges or grooves are created in the film. In one preferred embodiment, the ridges and grooves are exposed on the top and bottom surface of the protector film in order to maintain as thin a film as possible; however, it is contemplated that the top could be formed having a smooth surface or covered by an additional smooth film. The base member has perforations passing from the upper surface through to the lower surface thereof. The lower surface of the base member is coated with an adhesive layer which is appropriate for removably adhering the base member to a user's skin. The base member is removably adhered to a release paper substrate by the adhesive coating and the adhesive is water resistant.

It is an object of this invention to provide a device which protector s and protects the nipples of a user from the rubbing and chafing from a piece of apparel worn on the upper torso which occurs at times when the user is particularly active such as during exercise or sports activities.

It is an object of this invention to provide a device which protector s and protects the nipples of a user from the rubbing and chafing without the inclusion of a central pad which causes an outward protrusion from the application cite.

It is an object of this invention to provide a device which protector s and protects the nipples of a user from the rubbing and chafing wherein the device is transparent and therefore blends in with the color of the skin of the user, especially for a user who chooses not to wear a garment on the upper torso.

It is an object of this invention to provide a device which protector s and protects the nipples of a user which is transparent and blends in with the color of the skin of the user.

It is an object of this invention to provide a device which protector s and protects the nipples of a user which is air permeable to allow the skin protector ed by the device to breath normally and not be discolored with use.

It is an object of this invention to provide a device which protector s and protects the nipples of a user which comprises a material which is non-allergenic.

It is an object of this invention to provide a device which protector s and protects the nipples of a user which is easy to use and inexpensive to manufacture.

It is an object of the invention to provide a protective cover which upon application prevents the nipple from protruding.

It is an object of the invention to provide a protective cover which removably adheres to a user's skin and is peelable therefrom.

It is an object of the invention to provide an adhesive protector which resists water. It is an object of the invention to provide a semi-transparent or translucent protector.

It is an object of the invention to utilize a polymer to which a dye or colorant can be added to tint or shade the protector in a desired cover.

It is an object of the present invention to provide a discrete, breathable, and sweat resistant nipple protector to prevent nipple chafing.

It is an object of the present invention to provide a nipple protector which helps to conceal nipples under lightweight or clingy tops, bras, tanks, tees providing a modest look without revealing layers or padding.

It is an object of the present invention to provide a nipple protector that is transparent, breathable and water resistant.

It is an object of the present invention to prevent chafing and irritation caused from extended physical activities such as long distance running Other objects, features, and advantages of the invention will be apparent with the following detailed description taken in conjunction with the accompanying drawings showing a preferred embodiment of the invention.

BRIEF DESCRIPTION OF THE DRAWINGS

A better understanding of the present invention will be had upon reference to the following description in conjunction with the accompanying drawings in which like numerals refer to like parts throughout the several views and wherein.

DESCRIPTION OF THE PREFERRED EMBODIMENTS

Figure 1:
FIG. 1 is a perspective view of a runner wearing the nipple abrasion patch shown as broken lines depicting the structure beneath a jersey.

FIG. 1 shows a runner wearing a nipple abrasion patch or protector 10 show as broken lines depicting the structure beneath a jersey.

Figure 2:
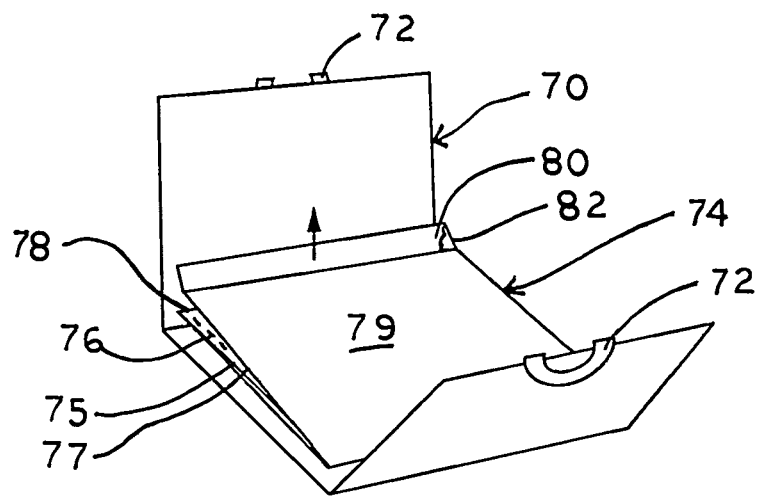
FIG. 2 is a perspective view of the tri-fold envelope sealed with an adhesive disc or ring which includes a package of the nipple abrasion protectors wherein the package comprises a doubled over sheet of heavy stiff paper or cardboard material having a removable adhesive around at least selected points at the periphery edge of the doubled over sheets forming a sealable envelope which breaks open to expose a sheet of nipple protectors, and the doubled over sheets including a third perforated flap projected from the distal end of one of the free sheets which doubles over the outside edge of the sheet securing the distal ends of the doubled over sheets together with a tacky or releasable adhesive.

As best shown in FIG. 2, the protector patch 10 is contained in a sealable tri-fold envelope 70 sealed with an adhesive disc or ring 72 which includes one or more sheets 11 of the nipple abrasion protectors within a resealable package 74 disposed therein. The resealable package 74 comprises a doubled over sheet of paper or cardboard material having a removable adhesive 76 around at least selected points at the inner peripheral edges 75, 77 of the doubled over sheets 78, 79 forming a resealable envelope 74 which breaks open to expose a sheet of nipple protectors 10. The doubled over sheets including a third perforated flap 80 projecting from the distal end of one of the free sheets 78 which doubles over the outside edge of the sheet securing the distal ends of the doubled over sheets together with a tacky or releasable adhesive 82.

Figure 3:
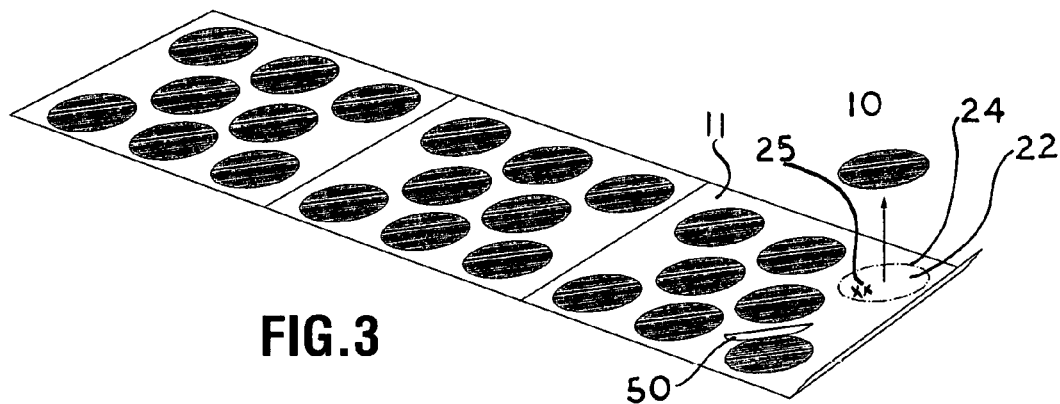
FIG. 3 shows an spread sheet view of the package held within the doubled over sheets in an unfolded state, showing the individual nipple protectors releasably and adhesively secured to the backside of the package comprising a tri-folded sheet of paper or film coated with a releasable substrate in order to facilitate removal of the protectors from the sheet backing, wherein the peelable tab is shown covering the nipple protectors.

A spread sheet showing the protector containing sheets 11 in FIG. 3 show the doubled over sheets in an unfolded state and the individual nipple protectors releasably and adhesively secured to the backside of the sheets 11 comprising a tri-folded sheet of paper or film coated with a releasable adhesive substrate in order to facilitate removal of the protectors from the sheet wherein the peelable tab 12 is shown covering the nipple protectors 10.

Figure 4:
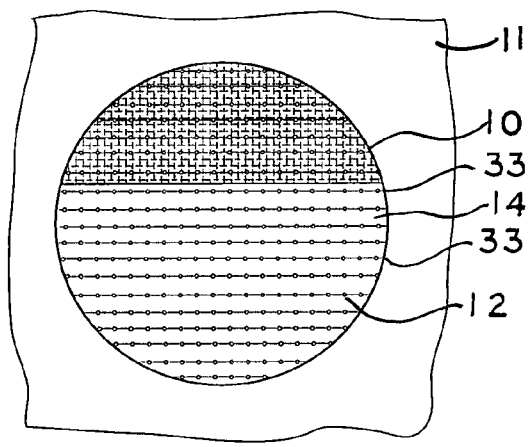
FIG. 4 is a top view of a nipple protector showing the film having air pores extending there through on the lower portion of the drawing and showing the pull tab cover removably secured to the bottom surface of the upper portion of the nipple protector by a releasable adhesive forming a flap for gripping.
Figure 5:
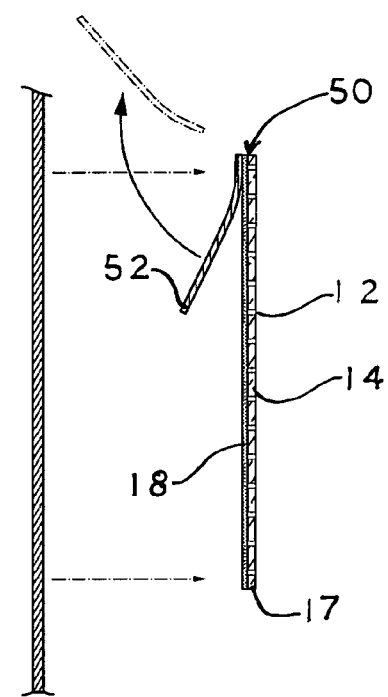
FIG. 5 is a side view showing removal of the flap or pull tab from the inner surface of the nipple protector from the adhesive backing and showing the top layer of film.
Figure 6:
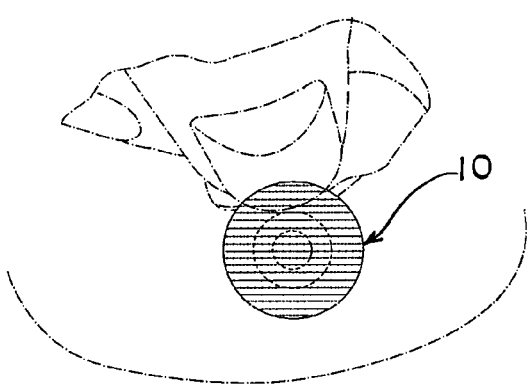
FIG. 6 is a perspective view showing the nipple protector covering the nipple of a wearer held in position by a releasable adhesive.
Figure 7:
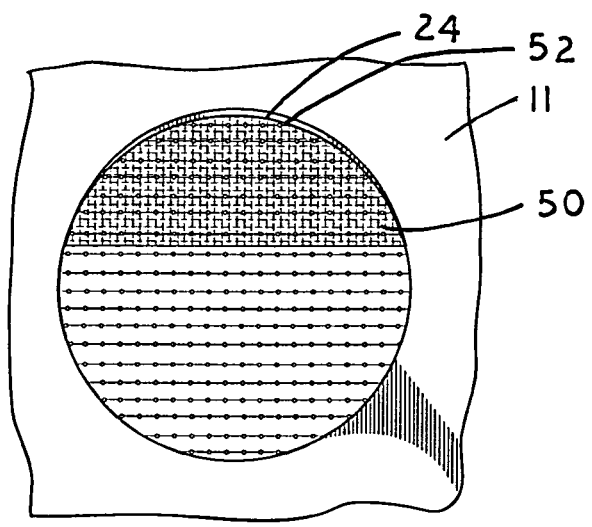
FIG. 7 shows the nipple protector wherein the upper portion comprises the pull flap having a film or peelable paper attached to the underside surface thereof and the bottom portion showing a portion of the flap releasably secured to the coated backing of the spread sheet.
Figure 8:
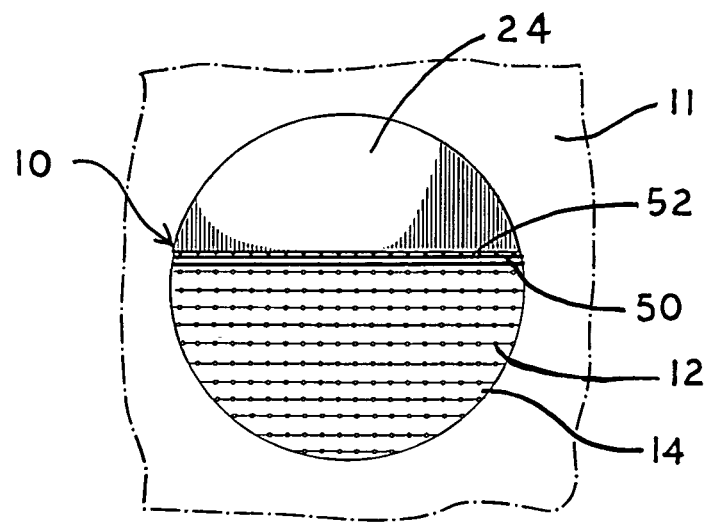
FIG. 8 shows a the nipple protector wherein the upper portion comprises the pull flap having a film or peelable paper attached to the underside surface thereof wherein the flap is pulled straight up showing the outline of the paper backing and the bottom portion showing the top surface of the nipple protector which is releasably secured to the paper backing by a selected releasable adhesive.

FIGS. 4 and 7-8 show the nipple protector or base member 10 having air pores or perforations 12 extending there through and a pull tab 50 formed by a cover 52 comprising a peelable film or paper removably secured to a portion of the bottom surface of the nipple protector by a releasable adhesive forming a flap for gripping with the portion of the protector not covered by the cover being releasably secured to the sheet 11. The pull tab provides a means of gripping the nipple protector and for removal from the surface of sheet 11. The adhesive containing portion of the protector 10 is aligned and applied onto the nipple and the cover 52 is peeled away from the pull tab portion 50 of the nipple protector allowing application of same to the nipple without having to touch the adhesive portion of the protector with ones fingers. As shown in FIGS. 7 and 8 the pull tab or flap 50 is attached to the bottom of the protector and between the protector and sheet 11.

FIG. 8 shows a the nipple protector wherein the pull tab 50 is standing at a right angle to the sheet backing 11 showing the film or peelable paper cover 52 attached to the underside surface of the protector 10.

In accordance with the present invention, there is provided a nipple protector 10 in the shape of a disc with a preferable thickness 16 of about one half of a millimeter. Nipple protector 10 has perforations 12 to provide breathability so that the skin underneath doesn't discolor while wearing the nipple protector. FIG. 1 shows that one perforation 12, has been incised during the cutting process in which the disc 10 was cut from a continuous piece of tape. The cross hatched ridges 14 on the bottom surface 17 help to make the nipple protector flexible and pliable. An adhesive layer 18 is applied to the bottom surface. The material used in making the nipple protector 10 is non-allergenic and flexible.

The protector comprises an adhesive film having indentations formed by creasing the film with closely spaced apart parallel ridges in a selected orientation. For example, spaced apart parallel ridges 14 are formed having channels 33 there between including a plurality of pores 12 formed therein as best shown in FIGS. 4-8.

The adhesive 18 is water proof and sweat proof. Adhesive 18 sticks tightly enough so that the disc is not pulled or rubbed off by the friction of a moving garment. However, the nipple protector 10 can be removed without causing discomfort to the nipples or the surrounding area.

The nipple protector is made from the same materials as those used in medical bandages and tapes. Among materials that are used in the manufacture of medical tapes, there is an increased use of polyolefins. This category of materials includes polystyrene, polycarbonate, acrylics, silicone rubber, polyethylene, polypropylene, and synthetic rubbers. Each of these materials has its own benefits and limitations, and must be carefully matched with the appropriate adhesive. For example, "non-stick" Low Surface Energy (LSE) plastics, such as polyethylene and polypropylene, require new adhesives specifically designed for strong bonding. The primary types of adhesives used in these applications include acrylics, epoxies, silicones, and styrene block co-polymers.

As shown in FIG. 2, several nipple protectors 10 are removably attached to release paper strip. The upper surface 22 of release paper strip 24 comprises a surface which will only slightly adhere to adhesive 18. The upper surface 22 is coated with wax or other release agent 25.

The foregoing detailed description is given primarily for clearness of understanding and no unnecessary limitations are to be understood therefrom, for modification will become obvious to those skilled in the art upon reading this disclosure and may be made upon departing from the spirit of the invention and scope of the appended claims. Accordingly, this invention is not intended to be limited by the specific exemplification presented herein above. Rather, what is intended to be protected is within the spirit and scope of the appended claims.

I claim:

1. A nipple protector for protection from chafing consisting essentially of:
   a flexible and pliable disc-shaped base member of a selected size for covering a nipple and at least a portion of an areola, said disc-shaped base member including a plurality of spaced apart ridges formed on a bottom surface thereof;
   said disc-shaped base member including a plurality of perforations formed therein disposed in between said plurality of spaced apart ridges forming air passages there through from a top surface to said bottom surface;
   an adhesive coating applied to said bottom surface of said disc-shaped base member for removable attachment to a release substrate and removable attachment to and detachment from a skin of a user.

2. The nipple protector defined in claim 1 wherein said base member comprises a polymer selected from a group consisting of a polystyrene, a polyethylene, a silicone, a polyvinyl chloride, a silicone rubber, a polyethylene, a polypropylene, a synthetic rubber elastomer, and combinations thereof.

3. The nipple protector defined in claim 1 wherein said adhesive is selected from the group consisting of acrylics, epoxies, silicones, and styrene block co-polymers.

4. The nipple protector of claim 1, wherein said plurality of perforations are formed between a first spaced apart parallel ridges and a second set of spaced apart parallel ridges.

5. A nipple protector for protection from chafing comprising:
   a flexible and pliable disc-shaped base member of a selected size for covering a nipple and an areola, said disc-shaped base member including a plurality of spaced apart ridges formed on a bottom surface thereof;
   said disc-shaped base member including a plurality of perforations formed therein disposed between said plurality of spaced apart ridges forming air passages there through from a top surface to said bottom surface;
   an adhesive coating applied to said bottom surface of said disc-shaped base member for removable attachment to a release substrate and removable attachment to and detachment from said nipple and said areola of a user; and
   a removable cover adhering to an adhesive on said bottom surface of said disc-shaped base member forming a pull tab for removing said nipple protector from said sheet a release paper strip.

6. The nipple protector of claim 5, wherein said plurality of spaced apart ridges comprise at least a first set of spaced apart parallel ridges and at least a second set of spaced apart parallel ridges.

7. The nipple protector of claim 6, wherein said plurality of perforations are formed between said first set of spaced apart parallel ridges and said second set of spaced apart parallel ridges.

8. A nipple protector comprising:
   a flexible and pliable round base member of a selected size for covering a nipple and at least a portion of an areola, said disc-shaped base member including a plurality of spaced apart ridges formed on a bottom surface thereof;
   said round base member including a plurality of perforations formed therein disposed in between said plurality of spaced apart ridges forming air passages there through from a top surface to said bottom surface;
   an adhesive coating applied to said bottom surface of said disc-shaped base member for removable attachment to a release substrate and removable attachment to and detachment from said nipple and said areola of a user;
   said release substrate comprising a paper coated with a release agent.

9. The nipple protector of claim 8, wherein said release agent is a wax coating.

10. The nipple protector of claim 8, wherein said round base member is transparent.

11. The nipple protector of claim 8, wherein said round base member is air permeable.

12. The nipple protector of claim 8, including a pull tab covering at least a portion of said round base member for removing said round base member from said release substrate.

13. The nipple protector of claim 8, wherein said round base member comprises a polymer.

14. The nipple protector of claim 8, wherein said round base member is non-allergenic.

\* \* \* \* \*